United States Patent [19]

Lukasiewicz

[11] Patent Number: 4,709,704
[45] Date of Patent: Dec. 1, 1987

[54] MONITORING DEVICE FOR BIO-SIGNALS

[75] Inventor: Mark Lukasiewicz, New City, N.Y.

[73] Assignee: The Kendall Company, Walpole, Mass.

[21] Appl. No.: 900,267

[22] Filed: Aug. 26, 1986

Related U.S. Application Data

[63] Continuation of Ser. No. 586,658, Mar. 6, 1984, abandoned.

[51] Int. Cl.⁴ .............................................. A61B 5/04
[52] U.S. Cl. .................................... 128/644; 128/693; 128/734; 128/903
[58] Field of Search ............................... 128/639–641, 128/644, 670, 671, 693, 713, 734, 798, 802, 903, 380, 385; 340/573

[56] References Cited

U.S. PATENT DOCUMENTS

| | | | |
|---|---|---|---|
| 2,433,233 | 12/1947 | Meminger | 128/380 |
| 3,910,257 | 10/1975 | Fletcher | 128/640 |
| 3,943,918 | 3/1976 | Lewis | 128/640 |
| 4,129,125 | 12/1978 | Lester et al. | 128/671 |
| 4,202,344 | 5/1980 | Mills et al. | 128/644 |
| 4,411,267 | 10/1983 | Heyman | 128/385 |

OTHER PUBLICATIONS

Kubicek et al., "Development . . . Cardiac Output System", Aerospace Med, 37, p. 1208–1212, 1966.
Meinrath et al., "Anonobttruswe Heart Rate Elementary System . . .", Behavior Res Meth& Inst., 1977, vol. 9, (3), 243–246.

Primary Examiner—Lee S. Cohen
Attorney, Agent, or Firm—James W. Potthast

[57] ABSTRACT

A monitoring device comprising, a belt having a sufficient length for placement around a patient's body, a conductive electrode on the belt for contacting the patient's skin, and a device for securing the belt about the patient's body. The monitoring device has a transmitter of electromagnetic waves connected to the belt and electrically connected to the electrode in order to transmit bio-signals from the patient's body.

2 Claims, 3 Drawing Figures

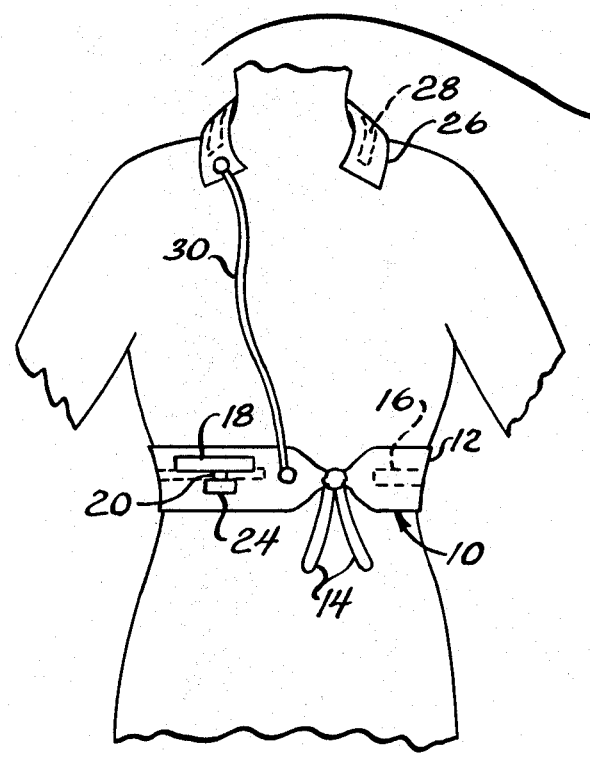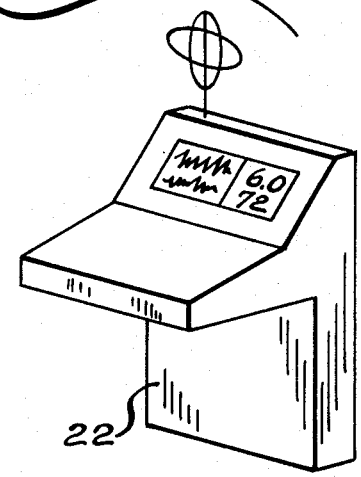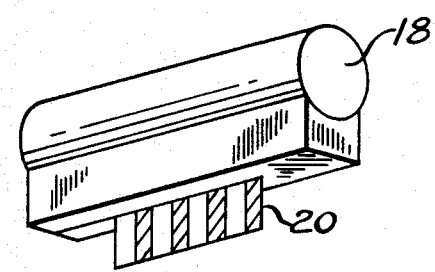
FIG. 1
FIG. 2

MONITORING DEVICE FOR BIO-SIGNALS

This application is a continuation of application Ser. No. 06/586,658, filed Mar. 6, 1984, now abandoned.

BACKGROUND OF THE INVENTION

The present invention relates to portable monitoring devices for bio-signals.

Before the present invention, a number of electrodes have been proposed for detecting signals in a patient. One of the problems with known monitors is that the neck electrodes used therewith had to be pressed against the patient's throat. However, the electrodes normally have conductive leads connected to a monitor, which in the case of impedance plethysmography results in interlead capacitance and affects the signals. Also, the weight of the leads on the electrodes results in motion artifacts and thus affects the signals.

SUMMARY OF THE INVENTION

A principal feature of the present invention is the provision of an improved monitoring device for bio-signals which overcomes the problems of known monitors and does not require any pressure against the patient's throat.

The device of the present invention comprises, a belt having a sufficient length for placement around a patient's body, and a conductive abdominal electrode on the belt for contacting the patient's skin together with an open collar electrode assembly for containing the back of the patient's neck. The device has means for securing the belt about the patient's body while the neck electrode is held in place partly by end portions which are draped over the patient's shoulders. The device also has a transmitter of electromagnetic waves connected to the belt and electrically connected to the electrode in order to transmit bio-signals from the patient's body generated by both the abdominal electrode and the neck electrode.

A feature of the present invention is that the monitoring device eliminates conductive leads which are normally connected to the electrode.

Another feature of the invention is that for an impedance plethysmograph the device eliminates interlead capacitance.

Still another feature of the invention is that the device eliminates the weight of conductive leads on the electrodes and thus minimizes motion artifacts.

Thus, a feature of the invention is that the device results in improved signals from the patient.

Still another feature of the invention is that the device may transmit multiple bio-signals from the patient's body.

Further features will become more fully apparent in the following description of the embodiments of this invention and from the appended claims.

DESCRIPTION OF THE DRAWINGS

In the drawings:

FIG. 1 is a perspective view of a monitoring device of the present invention; and FIG. 2 is a perspective view of a transmitter for the device of FIG. 1.

DESCRIPTION OF THE PREFERRED EMBODIMENTS

Referring now to FIGS. 1 and 2, there is shown a portable bio-information monitoring device generally designated 10 for the transmission of bio-signals from a patient's body.

The device 10 has an abdominal belt electrode assembly with an elongated abdominal belt 12 with a sufficient length to extend around the patient's body, with a pair of ties 14 adjacent opposed ends of the belt 12 for securing the belt 12 around the patient's body adjacent the xiphoid process.

The abdominal belt 12 has an elongated conductive electrode 16 for contacting the skin of the patient to receive a bio-signal from the abdominal region of the patient's body. The electrode 16 may be constructed from an aluminized mylar, a conductive gel, or a conductive adhesive.

The device 10 has a battery powered frequency modulation (FM) transmitter 18 which is releasably attached by a connector 20 to the belt 12. The transmitter 18 is electrically connected to the electrode 16 in order to transmit the bio-signals from the patient's body to a remote frequency modulation (FM) receiver 22. The device 10 may have processing equipment 24 on the belt 12, such as a demodulator and amplifier in order to process the bio-signals such that they are more compatible for transmission to the receiver 22.

The device 10 also has an open collar or neck electrode assembly with an elongated backing 26, such as foam, at an intermediate vertical portion thereof between with elongate end portions of sufficient length to extend around the neck back of the of the patient and draped onto the opposed shoulders. The intermediate portion of the backing 26 has an elongated conductive electrode 28 at the intermediate portion for contacting the patient's skin about the patient's neck. The device also has a elongate conductive lead 30 electrically connecting the electrode 28 to the transmitter 18 which also transmits bio-signals from the electrode 28. The electrode 28 may be constructed from the same materials as the electrode 16.

Thus, in accordance with the present invention, the device 10 eliminates leads which are normally connected between the electrodes and a monitor. In this manner, for impedance plythysmography the device 10 eliminates interlead capacitance in order to obtain better signals. Also, the device 10 eliminates the normal weight of leads on the electrode in order to minimize motion artifacts and obtain an improved signal. Most importantly, it also eliminates any restriction about the patient's throat but still secures the neck electrode for support in an upright position.

The foregoing detailed description is given for clearness of understanding only, and no unnecessary limitations should be understood therefrom, as modifications will be obvious to those skilled in the art.

I claim:

1. A portable bio-information monitoring device, comprising:

a signal processing unit for converting neck and abdominal electrode signals applied to a pair of inputs thereof to a single composite signal containing bio-information suitable for radio transmission thereof;

an FM radio transmitter having an input coupled to the output of the signal processing unit for transmitting radio waves containing the bio-information of the composite signal;

an open collar electrode assembly for producing a neck electrode signal including an elongate, flexible open collar having an intermediate portion adapted to be held in a upright position against the back of the patient's neck when the patient is standing or sitting upright and elongate end portions at opposite sides thereof, said portions being of sufficient length to be drapable over and at least partially supportable by the opposite shoulders of the patient when the patient is standing or sitting upright and having free ends spaced from one another at the patient's throat to preclude any restriction of the patient's throat and to facilitate attachment and removal of the collar electrode assembly, an elongate, flexible neck electrode carried by said open collar at an inner surface thereof for making electrical contact with a patient's neck, and an elongate lead attached to the collar to be supported thereby and connected to the neck electrode, said lead having sufficient length for extending downwardly from the collar to the patient's abdominal area for connection with an input to said signal processing unit carried thereat; and an abdominal belt electrode assembly for producing an abdominal electrode signal including, an elongate, flexible abdominal belt of sufficient length for placement around a patient's abdominal region, an elongate, flexible, belt electrode carried by said belt at an inside surface thereof for making electrical contact with a patient's back, means for attaching the signal processing unit and the radio transmitter to the abdominal belt to be carried thereby with an input of the signal processing unit connected with the belt electrode, and a connector connected with the elongate lead carried by the belt at an outside surface thereof and coupled to another input of the signal processing unit for connection of said other input with the neck electrode through said elongate lead.

2. The device of claim 1 wherein the transmitter is releasably attached to the belt.

* * * * *